(12) United States Patent
Jin et al.

(10) Patent No.: US 11,567,050 B2
(45) Date of Patent: Jan. 31, 2023

(54) HYDROGEN SENSOR AND PREPARATION METHOD THEREFOR, AND METHOD FOR IMPLEMENTING HYDROGEN DETECTION

(71) Applicant: SUN YAT-SEN UNIVERSITY, Guangzhou (CN)

(72) Inventors: Chongjun Jin, Guangzhou (CN); Yang Shen, Guangzhou (CN); Xiaoyi She, Guangzhou (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 789 days.

(21) Appl. No.: 16/498,748

(22) PCT Filed: Dec. 13, 2017

(86) PCT No.: PCT/CN2017/115826
§ 371 (c)(1),
(2) Date: Sep. 27, 2019

(87) PCT Pub. No.: WO2019/085166
PCT Pub. Date: May 9, 2019

(65) Prior Publication Data
US 2021/0109070 A1     Apr. 15, 2021

(30) Foreign Application Priority Data
Nov. 2, 2017 (CN) .......................... 201711064216.4

(51) Int. Cl.
*G01N 33/00* (2006.01)
*G01N 21/552* (2014.01)
*G01N 21/77* (2006.01)

(52) U.S. Cl.
CPC ......... *G01N 33/005* (2013.01); *G01N 21/554* (2013.01); *G01N 21/77* (2013.01)

(58) Field of Classification Search
CPC .... G01N 33/005; G01N 21/554; G01N 21/77; G01N 2021/7773; G01N 2021/7783; G01N 21/69
See application file for complete search history.

(56) References Cited

U.S. PATENT DOCUMENTS 9,638,633 B2   5/2017 Kasemo et al.
9,846,146 B2  12/2017 Noh et al.
(Continued)

FOREIGN PATENT DOCUMENTS

CN   103196867 A    7/2013
CN   103336036 A   10/2013
(Continued)

OTHER PUBLICATIONS

First Search Report for Chinese Application No. 2017110642164 dated Apr. 19, 2019, 3 pages.
(Continued)

*Primary Examiner* — David P Porta
*Assistant Examiner* — Gisselle M Gutierrez
(74) *Attorney, Agent, or Firm* — Seyfarth Shaw LLP

(57) ABSTRACT

A hydrogen sensor and preparation method therefor, and a method for implementing hydrogen detection based on the hydrogen sensor. The hydrogen sensor includes an elastomeric substrate and a hydrogen sensitive material-based nanostructure positioned on the elastomeric substrate, the surface of the elastomeric substrate close to the hydrogen sensitive material-based nanostructure has a nanoarray structure, and the hydrogen sensitive material-based nanostructure and the nanoarray structure are complementary to each other. In addition, the present disclosure provides a preparation method for the hydrogen sensor and a method for implementing hydrogen detection based on the hydrogen sensor.

8 Claims, 8 Drawing Sheets

(56) References Cited

U.S. PATENT DOCUMENTS

| | | | |
|---|---|---|---|
| 2006/0204794 A1 | 9/2006 | Kikuchi et al. | |
| 2007/0285843 A1* | 12/2007 | Tran | B82Y 10/00 |
| | | | 360/245.9 |
| 2015/0323494 A1* | 11/2015 | Tran | G01N 27/4146 |
| | | | 506/13 |
| 2016/0123878 A1* | 5/2016 | Zayats | G01N 21/554 |
| | | | 356/445 |
| 2018/0217117 A1* | 8/2018 | Tran | G11C 13/04 |
| 2021/0102924 A1* | 4/2021 | Jin | G01N 21/47 |

FOREIGN PATENT DOCUMENTS

| | | |
|---|---|---|
| CN | 103424441 A | 12/2013 |
| CN | 104076066 A | 10/2014 |
| CN | 104502421 A | 4/2015 |
| CN | 105510311 A | 4/2016 |
| CN | 106053540 A | 10/2016 |
| CN | 106104257 A | 11/2016 |
| CN | 106959272 A | 7/2017 |
| CN | 107132253 A | 9/2017 |

OTHER PUBLICATIONS

Yusin Pak, "Palladium Nanoribbon Array for Fast Hydrogen Gas Sensing with Ultrahigh Sensitivity," Advanced Materials, Oct. 6, 2015, pp. 6945-6952, vols. 27, 43.

Sadullah Ozturk, "Pd thin films on flexible substrate for hydrogen sensor," Journal of Alloys and Compounds, Mar. 8, 2016, pp. 179-184 vol. 674.

\* cited by examiner

HYDROGEN SENSOR AND PREPARATION METHOD THEREFOR, AND METHOD FOR IMPLEMENTING HYDROGEN DETECTION

CROSS REFERENCE TO RELATED APPLICATIONS

This is a U.S. National Stage application of, and claims priority to, PCT/CN2017/115826, filed Dec. 13, 2017, which further claims priority to Chinese Patent Application No. 201711064216.4 filed Nov. 2, 2017, the disclosures of which are incorporated herein by reference in their entirety.

TECHNICAL FIELD

The present disclosure relates to a technical field of sensors, and more particularly, to a hydrogen sensor and a manufacturing method thereof, and a method for implementing hydrogen detection using the hydrogen sensor.

BACKGROUND

As a clean renewable energy carrier, hydrogen is considered as an ideal energy source to replace conventional fossil fuels. With the continuous development of hydrogen fuel cell technology, how to ensure that the hydrogen is produced, stored and used safely and efficiently has become a key issue for stepping into the era of "hydrogen economy". However, hydrogen has an extremely wide explosion limit (bulk density of 4%-75%) and a very low ignition energy (0.02 mJ). Therefore, a hydrogen sensor is very necessary for hydrogen application.

The hydrogen sensor mainly includes sensors sensed with electricity and optical hydrogen sensors. The optical sensors mainly include surface plasmon sensors and sensors with film structure. A surface plasmon hydrogen sensor is mainly based on a plasmon resonance effect of metal nanoparticles or nanostructures. At a resonant wavelength of the hydrogen-sensitive metal nanoparticles, the incident light can be restricted in a region with sub-wavelength size near the surface of metal. When the hydrogen-sensitive metal nanoparticles absorb hydrogen, it will transform from a metal state to a metal hydride state, and its dielectric constant will change accordingly, causing a shift of its resonant wavelength. The detection for hydrogen can be achieved by monitoring the resonant wavelength.

Generally, the surface plasmon optical hydrogen sensor is formed by forming metal nanoparticles or nanostructures on a rigid substrate, thereby limiting the volume expansion of hydrogen-sensitive metal nanostructure during hydrogen absorption, and the optical response induced by structural geometry is greatly reduced.

SUMMARY

Accordingly, as for the problem of how to improve the sensitivity of the hydrogen sensor, it is necessary to provide a hydrogen sensor and a manufacturing method thereof, and a method for implementing hydrogen detection using the hydrogen sensor.

A hydrogen sensor includes an elastic substrate and a hydrogen-sensitive material nanostructure positioned on the elastic substrate, a surface of the elastic substrate adjacent to the hydrogen-sensitive material nanostructure has a nanoarray structure, the hydrogen-sensitive material nanostructure and the nanoarray structure are complementary to each other.

In one of the embodiments, a material used in the hydrogen-sensitive material nanostructure is at least one selected from the group consisting of palladium, magnesium, yttrium, and nickel-magnesium alloy.

In one of the embodiments, the hydrogen-sensitive material nanostructure is selected from a one-dimensional nanoarray or a two-dimensional nanoarray.

In one of the embodiments, the hydrogen-sensitive material nanostructure is selected from a one-dimensional nano-groove array, and the hydrogen-sensitive material nanostructure has a period of 300 nm to 100000 nm.

In one of the embodiments, a groove in the one-dimensional nano-groove array has a depth of 50 nm to 1000 nm.

In one of the embodiments, a groove in the one-dimensional nano-groove array has an opening width of 150 nm to 400 nm.

In one of the embodiments, the elastic substrate includes a first elastic substrate and a second elastic substrate which are sequentially laminated, and a Young's modulus of the second elastic substrate is greater than a Young's modulus of the first elastic substrate.

In one of the embodiments, the first elastic substrate has a thickness of 0.5 mm to 10 mm, and the second elastic substrate has a thickness of 5 μm to 100 μM.

A manufacturing method of the hydrogen sensor as described above includes:

forming an adhesive film on a rigid substrate;

forming a photoresist layer on the adhesive film under a dark room condition, and treating the photoresist layer so that the photoresist layer has a nano-grating structure;

mixing and stirring a liquid elastic material and a curing agent uniformly to obtain a mixed liquid, and coating the mixed liquid on the nano-grating structure, and drying and curing the mixed liquid to obtain an elastic substrate;

peeling off the treated photoresist layer from the elastic substrate, and forming a nanoarray structure on the elastic substrate; and depositing a hydrogen-sensitive material on a surface of the elastic substrate having the nanoarray structure, and forming a hydrogen-sensitive material nanostructure.

A method for implementing hydrogen detection based on the hydrogen sensor as described above includes:

irradiating an incident light onto a surface of the hydrogen-sensitive material nano structure, and measuring an optical parameter of the hydrogen-sensitive material nano structure, the optical parameter being a resonant wavelength, a full width at half maximum value of resonant peak, a reflectivity, a reflected light intensity, a transmittivity, a transmitted light intensity, a scattering cross-section, an extinction cross-section, an absorption cross-section or an absorbance;

introducing a gas containing hydrogen, expanding the hydrogen-sensitive material nanostructure in volume after absorbing hydrogen, and deforming the elastic substrate;

irradiating the incident light onto a surface of the deformed hydrogen-sensitive material nanostructure, and measuring optical parameters of the deformed hydrogen-sensitive material nanostructure; and obtaining a change in a relative optical parameter according to optical parameters of the hydrogen-sensitive material nanostructure before and after deforming, and determining a concentration of hydrogen according to the change in the relative optical parameters.

According to the hydrogen sensor and the method for implementing hydrogen detection using the hydrogen sensor as described above, when the hydrogen-sensitive material nanostructure is in contact with hydrogen, the hydrogen-sensitive material nanostructure absorbs hydrogen, the hydrogen-sensitive material expands in volume, and applies stress to the surface of the elastic substrate during the expansion, causing a change in the geometry of the nanostructure of the elastic substrate. At the same time, the deformation of the elastic substrate also causes a change in the hydrogen-sensitive material nanostructure, so that the geometry of the hydrogen-sensitive material nanostructure is more fully deformed, and thus the shift amount of the resonant wavelength and the change in the relative reflectivity intensity of the hydrogen-sensitive material nanostructure are further amplified, and the sensitivity of the hydrogen sensor is improved.

The aforementioned manufacturing method of the hydrogen sensor is not only simple in manufacture, low in cost, but also widely applicable.

DETAILED DESCRIPTION OF THE EMBODIMENTS

Figure 1:
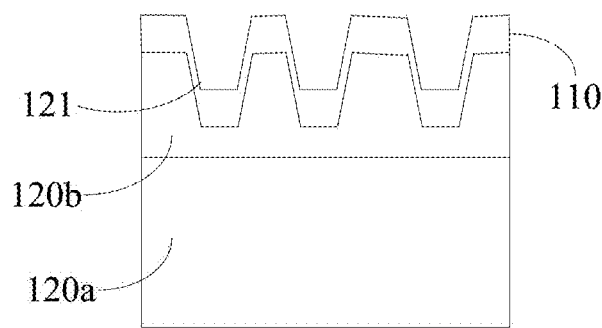
FIG. 1 is a schematic view showing a hydrogen sensor according to an embodiment.

In order to facilitate the understanding of the present disclosure, the present disclosure will be described more fully hereinafter with reference to the related attached drawings. Preferred embodiments are presented in the drawings. However, the present disclosure may be embodied in many different forms and is not limited to the embodiments described herein. Rather, these embodiments are provided so that the present disclosure will be understood more thoroughly and completely.

All technical and scientific terms used herein have the same meaning as commonly understood by skilled person in the art to which this disclosure belongs, unless otherwise defined. The terms used in the specification of the disclosure herein are only for the purpose of describing specific embodiments and are not intended to limit the present disclosure. The term "and/or" used herein includes any and all combinations of one or more of the associated listed items.

As shown in FIG. 1, a hydrogen sensor 100 according to an embodiment includes an elastic substrate and a hydrogen-sensitive material nanostructure 110. The hydrogen-sensitive material nanostructure 110 is positioned on the elastic substrate. A surface of the elastic substrate adjacent to the hydrogen-sensitive material nanostructure 110 has a nanoarray structure, and the hydrogen-sensitive material nanostructure and the nanoarray structure are complementary to each other. The hydrogen sensor 100 may be a surface plasmon optical sensor.

Therefore, when under a hydrogen atmosphere, and when the hydrogen-sensitive material nanostructure 110 is in contact with the hydrogen, the hydrogen-sensitive material nanostructure 110 absorbs hydrogen, the hydrogen-sensitive material expands in volume, and applies stress to the surface of the elastic substrate during the expansion, so that the geometry of the nanostructure of the elastic substrate changes. At the same time, the deformation of the elastic substrate also causes a change in the hydrogen-sensitive material nanostructure 110, so that the geometry of the hydrogen-sensitive material nanostructure 110 is more fully deformed, and the change in the relative reflectivity intensity and the shift amount of the resonant wavelength of the hydrogen-sensitive material nanostructure 110 are further amplified, and thus the sensitivity of the hydrogen sensor is improved. After dehydrogenating the hydrogen-sensitive material nanostructure 110, due to an elastic restoring force of the elastic substrate 110, the elastic substrate 110 returns to an initial state, causing the hydrogen-sensitive material nanostructure 110 to return to a smooth state, and thus the hydrogen sensor 110 returns to an initial state, so that the hydrogen sensor 100 may be used multiple times.

The conventional surface plasmon optical hydrogen sensor uses a rigid substrate, which not only limits the volume expansion of the hydrogen-sensitive metal nanostructure during hydrogen absorption, but also greatly reduces the optical response induced by the structural geometry, and also causes a relatively large scattering loss of localized plasmon, thus causes the resonance peak to have a relatively wide full width at half maximum, which reduces the sensing performance. In addition, a great stress is generated between the hydrogen-sensitive metal nanostructure and the rigid substrate during the hydrogen absorption of the hydrogen-sensitive metal nanostructure, which is easy to cause detachment, resulting in a decrease in the number of uses of the surface plasmon optical hydrogen sensor, thereby reducing its lifetime.

Compared with the conventional surface plasmon optical hydrogen sensor, the hydrogen sensor 100 has an elastic substrate, and the geometry of the hydrogen-sensitive metal nanostructure 110 on the elastic substrate is more fully deformed under a hydrogen atmosphere, thereby amplifying the change in the relative reflectivity intensity and the shift amount of the resonant wavelength of the hydrogen-sensitive material nanostructure 110, and the shift of its resonant wavelength may be up to 28 nm. Meanwhile, at a visible wavelength band, a change in the relative reflectivity intensity of the hydrogen-sensitive material nanostructure 110 may be up to 390%, and such a strong change in the relative reflectivity intensity may be directly observed by naked eyes. In addition, a propagation surface plasmon supported by the hydrogen-sensitive material nanostructure 110 interacts with its cavity mode to form a coupled resonant mode, thereby greatly reducing the full width at half maximum value for the reflection valley or peak, so that the full width at half maximum value of the resonance of the hydrogen-sensitive material nanostructure 110 may be as narrow as 32 nm. Moreover, due to the relatively small Young's modulus of the elastic substrate, the stress between the hydrogen-sensitive material nanostructure 110 and the elastic substrate during hydrogen absorption will be reduced, thereby decreasing the probability of the detachment of the hydrogen-sensitive material nanostructure 110 during hydrogen absorption, and the number of uses and lifetime of the hydrogen sensor 100 are increased.

In one of the embodiments, a material used in the hydrogen-sensitive material nanostructure 110 is at least one selected from the group consisting of palladium, magnesium, yttrium, and nickel-magnesium alloy. A palladium film can react well with hydrogen under an environment of ambient temperature and pressure. In the present embodiment, the material used in the hydrogen-sensitive material nanostructure 110 is palladium. It should be noted that the material used in the hydrogen-sensitive material nanostructure 110 may also be other metals or metal composites of which the volume will expand after absorbing hydrogen.

In one of the embodiments, the hydrogen-sensitive material nanostructure 110 is selected from a one-dimensional nanoarray or a two-dimensional nanoarray. It should be noted that the hydrogen-sensitive material nanostructure 110 is selected from a periodic nanoarray, but is not limited thereto. One-dimension means that the structure is periodic in one direction. The one-dimensional nanoarray may be a one-dimensional nano-groove array. In addition, the shape of a basic unit on the one-dimensional nanoarray may also be granular or other shapes. The two-dimensional nanoarray may be a two-dimensional nano-hole array.

Figure 2:
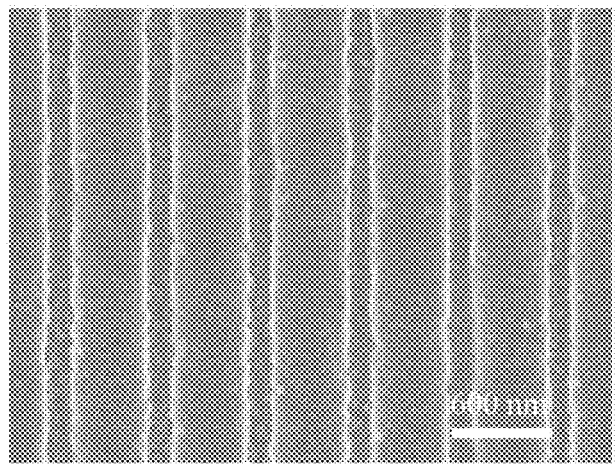
FIG. 2 is an scanning electron microscopy image of the hydrogen sensor of FIG. 1.
Figure 3:
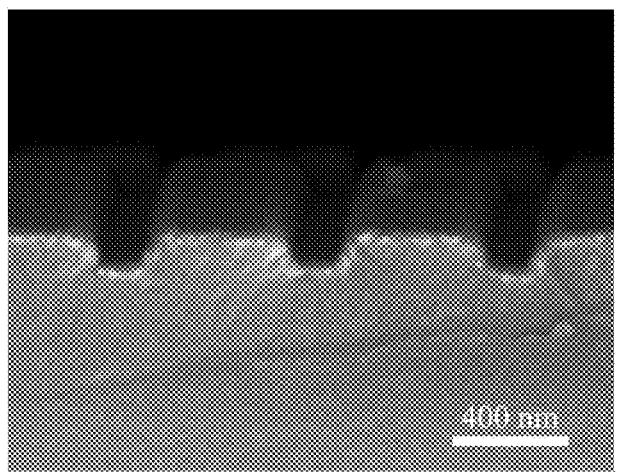
FIG. 3 is another scanning electron microscopy image of the hydrogen sensor of FIG. 1.

Further, the hydrogen-sensitive material nanostructure 110 is selected from the one-dimensional nano-groove array, and the hydrogen-sensitive material nanostructure 110 has a period of 300 nm to 100000 nm. In one embodiment, the hydrogen-sensitive material nanostructure 110 has a period of 400 nm to 1000 nm. In present embodiment, the hydrogen-sensitive material is selected from palladium. As shown in FIGS. 2 and 3, the hydrogen-sensitive material nanostructure 110 is also a nano-groove array.

In one of the embodiments, a groove in the one-dimensional nano-groove array has a depth of 50 nm to 1,000 nm. Particularly, the groove in the one-dimensional nano-groove array may have a depth of 90 nm.

In one of the embodiments, the groove in the one-dimensional nano-groove array has an opening width of 150 nm to 400 nm. Further, the shape of the cross-section of the groove in the one-dimensional nano-groove array is a trapezium, and the width thereof is gradually decreased from an opening of the groove to a bottom surface of the groove. In one of the embodiments, the groove in the one-dimensional nano-groove array has an opening width of 280 nm.

It should be noted that, by selecting the period of the one-dimensional nano-groove array, the depth of the grooves in the one-dimensional nano-groove array, and the opening width of the grooves in the one-dimensional nano-groove array, the resonant wavelength of the one-dimensional nano-groove array is changed, and thus the selection of the incident light is further expanded, so that incident light with various wavelengths may be selected.

In one of the embodiments, the Young's modulus of the elastic substrate is greater than 0 and less than or equal to 60000 MPa. The elastic substrate may be all the elastomers with low elastic modulus. The elastic substrate may be a thermoset elastomer and a thermoplastic elastomer. The thermoplastic elastomer may be a rubber such as styrene butadiene rubber, polybutadiene rubber, isoprene rubber, ethylene propylene rubber, butyl rubber, neoprene rubber, nitrile rubber or the like. The thermoplastic elastomer may also be a polyurethane-based thermoplastic elastomer, a polyamide-based thermoplastic elastomer, or a polyolefin-based thermoplastic elastomer. The thermoset elastomer may be polysiloxane, polyurethane, silicone rubber or the like. It should be noted that the elastic substrate is not limited thereto as long as the elastic substrate has elasticity. The polysiloxane may be polydimethylsiloxane.

Further, referring again to FIG. 1, in one of the embodiments, the elastic substrate includes a first elastic substrate 120a and a second elastic substrate 120b, which are sequentially laminated, and the Young's modulus of the second elastic substrate 120b is greater than the Young's modulus of the first elastic substrate 120a. Both the first elastic substrate 120a and the second elastic substrate 120b have good elasticity, and the second elastic substrate 120b has a higher Young's modulus and a higher resolution, so as to improve the accuracy of the subsequent formation of a template on the second elastic substrate 120b. And the Young's modulus of the first elastic substrate 120a is lower, so that the elasticity of the entire elastic substrate is improved. In one of the embodiments, the Young's modulus of the second elastic substrate 120b is 10 times more than the Young's modulus of the first elastic substrate 120b.

In one of the embodiments, the first elastic substrate 120a has a thickness of 0.5 mm to 10 mm, and the second elastic substrate 120b has a thickness of 5 μm to 100 μm. The first elastic substrate 120a has a greater thickness and mainly functions as providing an elastic force. It should be noted that in other embodiments, the elastic substrate may also only include the first elastic substrate 120a.

Referring again to FIG. 1, when the elastic substrate includes the first elastic substrate 120a and the second elastic substrate 120b, and the hydrogen-sensitive material nanostructure 110 is the one-dimensional nano-groove array, the hydrogen-sensitive material nanostructure 110 absorbs hydrogen and decomposes hydrogen into hydrogen atoms when exposed to a hydrogen atmosphere. The hydrogen atoms occupy the interstitial void of the hydrogen-sensitive material by diffusion, thus forming a hydride state of the hydrogen-sensitive material. Therefore, the dielectric constant of the hydrogen-sensitive material is changed, and the crystal lattice of the hydrogen-sensitive material expands, which causes the resonant wavelength of the hydrogen sensor to shift, so that the hydrogen concentration with low concentration may be detected by measuring the shift of resonant wavelength thereof or the change in the reflected light intensity.

In addition, the one-dimensional nano-groove array applies stress to a nano-groove interface of the second elastic substrate 120b during expansion, so that the geometry of the nano-groove on the second elastic substrate 120b changes (the opening size of the groove becomes smaller), thereby causing the resonant wavelength of the hydrogen-sensitive material nanostructure to shift further. The second elastic substrate 120b and the hydrogen-sensitive material nanostructure cooperate together, so that the resonant wavelength of the hydrogen sensor is greatly increased, thereby improving the sensing sensitivity of the hydrogen sensor.

The shift of the resonant wavelength of the hydrogen sensor may be up to 28 nm, and in the entire visible light region, the change in the relative reflectivity intensity thereof may exceed 390% under the action of 4% hydrogen concentration (mixed gas of hydrogen and nitrogen, the volume percentage of hydrogen is 4%). Such a strong change in relative reflectivity intensity may be directly observed by naked eyes. The sensor is low in cost, simple in manufacture, may be mass-produced, has high sensitivity and wide application, and is suitable for hydrogen detection in different environments.

Figure 4:
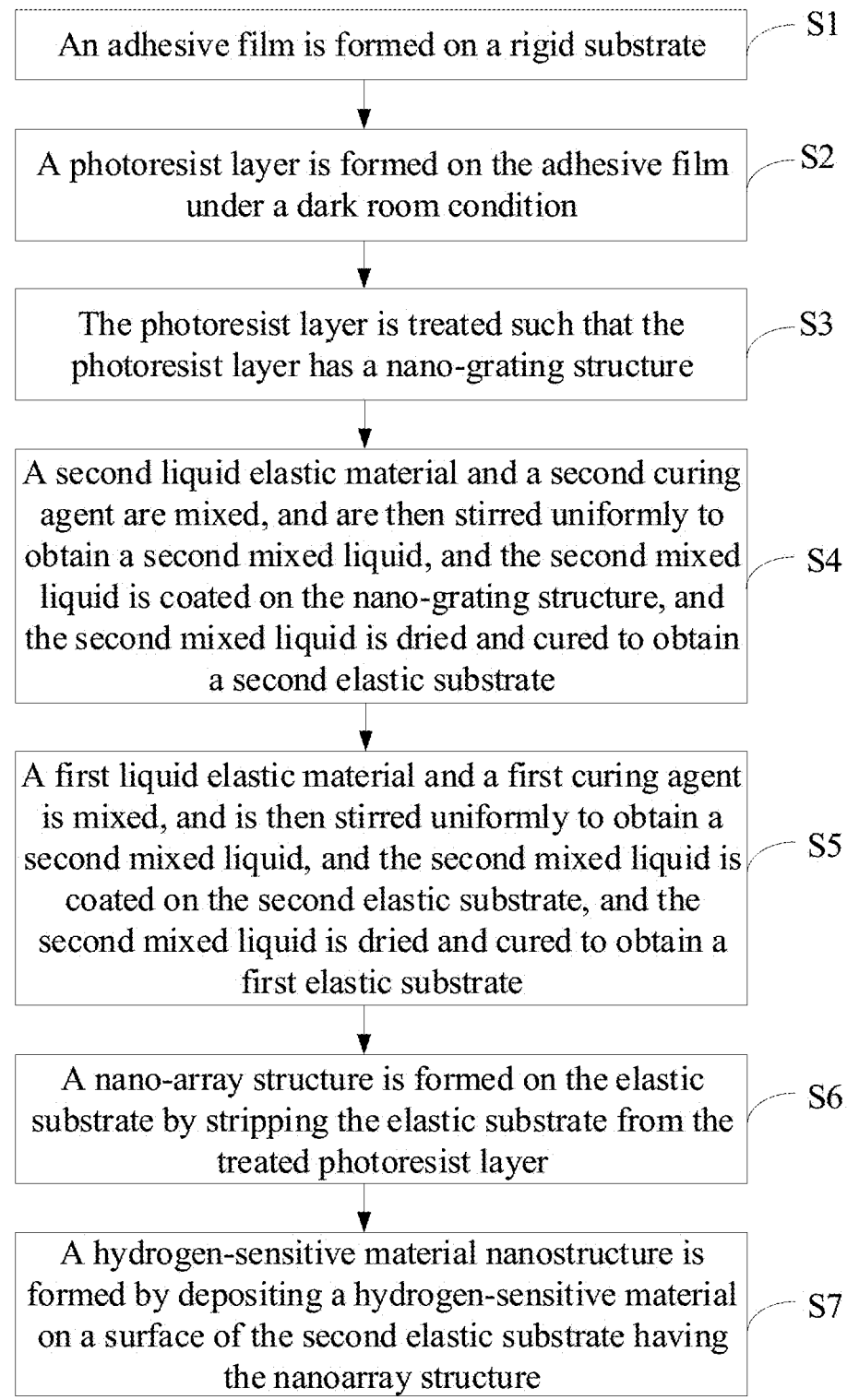
FIG. 4 is a flow chart of a manufacturing method of the hydrogen sensor according to embodiment.

As shown in FIG. 4, a manufacturing method of the hydrogen sensor according to an embodiment includes the following steps.

In step S1, an adhesive film is formed on a rigid substrate.

Figure 5:
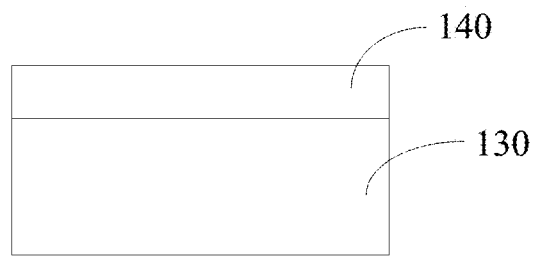
FIG. 5 is a schematic view showing an adhesive film formed on a rigid substrate.

Specifically, an adhesive film 140 is formed on a rigid substrate 130 by means of spin coating, as shown in FIG. 5. The rigid substrate 130 may be a transparent rigid substrate such as quartz or the like. The adhesive film 140 may be a polymethyl methacrylate film, a polyethylene film, or a polypropylene film. The adhesive film 140 may have a thickness of 30 nm to 200 nm in order to facilitate the subsequent formation of a photoresist layer.

In step S2, a photoresist layer is formed on the adhesive film under a dark room condition.

Figure 6:
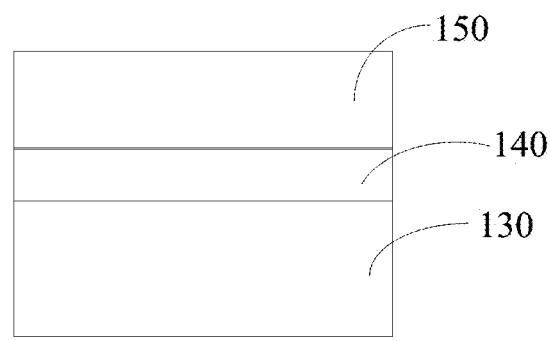
FIG. 6 is a schematic view showing a photoresist layer formed on the adhesive film of FIG. 5.

Specifically, as shown in FIG. 6, a photoresist layer 150 is formed on the adhesive film 140 by means of spin coating. The photoresist layer 150 may have a thickness of 80 nm to 600 nm. The photoresist used in the photoresist layer 150 is an AR-P 3740 high resolution positive photoresist (Allresist GmbH, Germany).

In step S3, the photoresist layer is treated so that the photoresist layer has a nano-grating structure.

Figure 7:
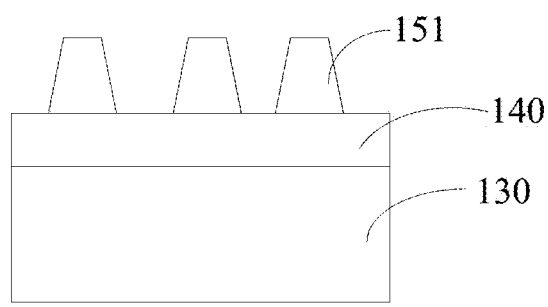
FIG. 7 is a schematic view showing the photoresist layer of FIG. 6 after being treated.

Specifically, a double beam exposure and development is performed on the photoresist layer 150, so that the photoresist layer 150 has a nano-grating structure 151. The nano-grating structure 151, the adhesive film 140, and the rigid substrate 130 cooperatively function as a template for molding, as shown in FIG. 7.

In addition, in order to facilitate the separation of the elastic substrate formed in the subsequent steps from the template, the template formed as described above and a release agent are placed together into a vacuum vessel, and vacuumizing and standing the vacuum vessel, so that the release agent molecules volatilize and cover on the template. The stand time may be 30 min to 60 min. The release agent may be selected from the group consisting of a siloxane compound, a silicone oil, a perfluorooctyltrichlorosilane and the like.

In step S4, a second liquid elastic material and a second curing agent are mixed and stirred uniformly to obtain a second mixed liquid, the second mixed liquid is coated on the nano-grating structure, dried and cured to obtain a second elastic substrate.

Figure 8:
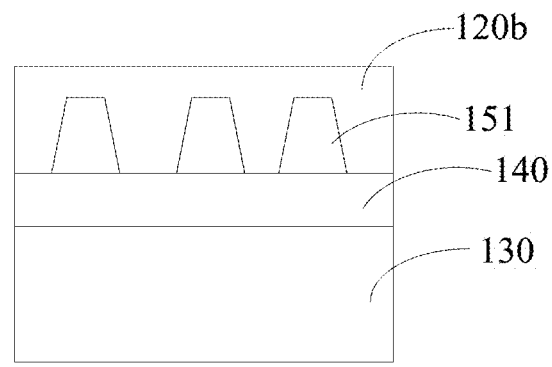
FIG. 8 is a schematic view showing a second elastic substrate formed on the photoresist layer of FIG. 7.

Specifically, the second liquid elastic material and the second curing agent are mixed and stirred uniformly, and then placed into the vacuum vessel for vacuumizing, and thus bubbles therein are removed, and thus the second mixed liquid is obtained. Next, the second mixed liquid is spin-coated on the template obtained in step S3, and then the template is placed into an oven for curing to form the second elastic substrate 120b on the template, as shown in FIG. 8. The second liquid elastic material may be a mixture of vinylmethylsiloxane-dimethylsiloxane copolymers, trimethylsiloxy terminated, 1,3,5,7-tetravinyltetramethylcyclotetrasiloxane, and tetramethyldivinylsiloxane platinum complex. The second curing agent may be a hydride terminated methyhydrosiloxane dimethylsiloxane copolymer. At this time, vinylmethylsiloxane-dimethylsiloxane copolymers, trimethylsiloxy terminated, 1,3,5,7-tetravinyltetramethylcyclotetrasiloxane, and tetramethyldivinylsiloxane platinum complex are firstly mixed with a certain ratio to obtain a mixture, and then the mixture is placed into the vacuum vessel for vacuumizing, and thus bubbles in the mixture are removed, and the bubble-removed mixture and the hydride terminated methyhydrosiloxane dimethylsiloxane copolymer are mixed to obtain the second mixed liquid. The mass of the vinylmethylsiloxane-dimethylsiloxane copolymers, trimethylsiloxy terminated, the 1,3,5,7-tetravinyltetramethylcyclotetrasiloxane, and the tetramethyldivinylsiloxane platinum complex may be 3.5 g, 100 mg, and 50 mg, respectively. The curing conditions may be: a temperature of 60° C. to 80° C. and a time of 10 to 20 minutes.

In step S5, a first elastic substrate is obtained by mixing and stirring a first liquid elastic material and a first curing agent uniformly to obtain a second mixed liquid, coating the second mixed liquid on the second elastic substrate, and drying and curing the second mixed liquid.

Figure 9:
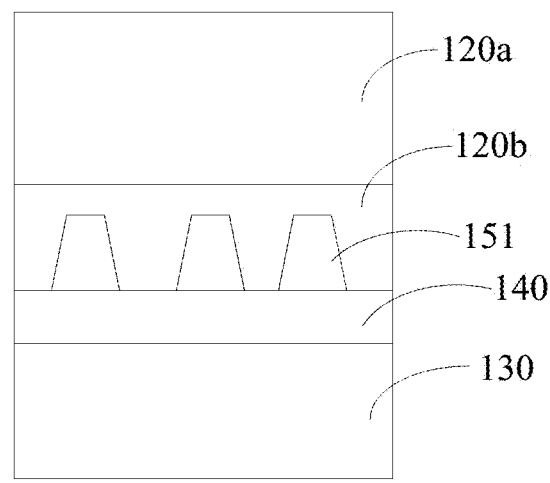
FIG. 9 is a schematic view showing a first elastic substrate formed on the second elastic substrate of FIG. 8.

Specifically, at a room temperature, the first liquid elastic material and the first curing agent are mixed at a ratio of 5:1 to 20:1, and then are stirred uniformly to obtain the second mixed liquid, and the second mixed liquid is coated on the second elastic substrate 120b, and is placed into a vacuum vessel for vacuumizing, and thus bubbles in the second mixed liquid are removed. Next, the template coated with the second mixed liquid is placed into an oven for drying and curing to form the first elastic substrate 120a, as shown in FIG. 9. The curing conditions may be: a temperature of 60° C. to 80° C. and a time of 10 to 20 minutes. In this embodiment, the first elastic material is polydimethylsiloxane (model: SYLGARD 184; manufacturer: Dow Corning, USA), and the first curing agent is silicone curing agent (model: SYLGARD 184; manufacturer: Dow Corning, USA).

In step S6, a nanoarray structure is formed on the elastic substrate after peeling off the elastic substrate from the treated photoresist layer.

Figure 10:
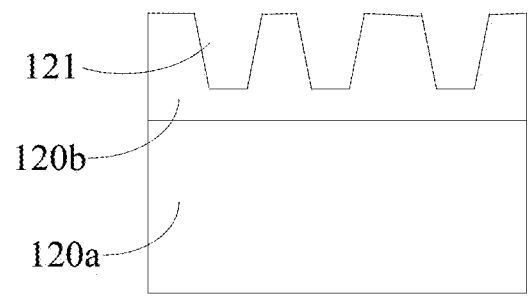
FIG. 10 is a schematic view showing the second elastic substrate of FIG. 8 after being separated from the photoresist layer.

Specifically, the first elastic substrate 120a and the second elastic substrate 120b positioning at the edge of the rigid substrate are cut open with a clean knife, and the second elastic substrate 120b is separated from the treated photoresist layer to form a composite elastic substrate having a nanoarray structure 121 on the second elastic substrate 120b, as shown in FIG. 10.

In step S7, a hydrogen-sensitive material nanostructure is formed by depositing a hydrogen-sensitive material on a surface of the second elastic substrate having the nanoarray structure.

Specifically, the hydrogen-sensitive material is deposited on the composite elastic substrate containing the nanoarray structure 121 obtained in step S6 by a magnetron sputtering apparatus, thus forming the hydrogen-sensitive material nanostructure 110, as shown in FIG. 1. In this embodiment, the hydrogen-sensitive material is palladium. The sputtering parameter may be 15 mA/240 s.

In another embodiment, the elastic substrate has a one-layer film structure. A manufacturing method of the hydrogen sensor according to another embodiment includes the following steps.

In step S10, an adhesive film is formed on a rigid substrate.

Specifically, a layer of adhesive film is formed on the rigid substrate by means of spin coating. The rigid substrate may be a transparent rigid substrate such as quartz or the like. The adhesive film may be a polymethyl methacrylate film, a polyethylene film or a polypropylene film. The adhesive film may have a thickness of 30 nm to 200 nm in order to facilitate the subsequent formation of a photoresist layer.

In step S20, a photoresist layer is formed on the adhesive film under a dark room condition.

Specifically, the photoresist layer is formed on the adhesive film by means of spin coating. The photoresist layer may have a thickness of 80 nm to 600 nm. The photoresist used in the photoresist layer 150 is AR-P 3740 high resolution positive photoresist (Allresist GmbH, Germany).

In step S30, the photoresist layer is treated so that the photoresist layer has a nano-grating structure.

Specifically, a double beam exposure and development are performed on the photoresist layer, so that the photoresist layer has the nano-grating structure. The nano-grating structure, the adhesive film, and the rigid substrate collectively function as a template for molding.

In addition, in order to facilitate the separation of the elastic substrate formed in the subsequent steps from the template, the template formed as described above and a release agent are placed into a vacuum vessel together, vacuumizing and standing the vacuum vessel, so that the release agent molecules volatilize and cover the template. The stand time may be 30 min to 60 min. The release agent may be selected from the group consisting of a siloxane compounds, a silicone oil and the like.

In step S40, an elastic substrate is obtained by mixing and stirring a liquid elastic material and a curing agent uniformly to obtain a mixed liquid, coating the mixed liquid on the nano-grating structure, and drying and curing the mixed liquid.

Specifically, at a room temperature, the liquid elastic material and the curing agent are mixed at a ratio of 5:1 to 20:1, and then are stirred uniformly to obtain the mixed liquid. The mixed liquid is coated on the photoresist layer having a nano-grating structure, and is placed into a vacuum vessel for vacuumizing, and thus bubbles in the mixed liquid are removed. Next, the template coated with the mixed liquid is placed into an oven for drying and curing to form an elastic substrate 1. The curing conditions may be: a temperature of 60° C. to 80° C. and a time of 10 to 20 minutes. In this embodiment, the first elastic material is polydimethylsiloxane (model: SYLGARD 184; manufacturer: Dow Corning, USA), and the first curing agent is silicone curing agent (model: SYLGARD 184; manufacturer: Dow Corning, USA).

In step S50, a nanoarray structure is formed on the elastic substrate after peeling off the elastic substrate from the treated photoresist layer.

Specifically, the elastic substrate positioned at the edge of the rigid substrate are cut open with a clean knife, and the elastic substrate is separated from the treated photoresist layer to form the nanoarray structure on the elastic substrate.

In step S60, a hydrogen-sensitive material nanostructure is formed by depositing a hydrogen-sensitive material on a surface of the elastic substrate having the nanoarray structure.

Specifically, the hydrogen-sensitive material is deposited on the elastic substrate containing the nanoarray structure obtained in step S50 by a magnetron sputtering apparatus, to form the hydrogen-sensitive material nanostructure. In this embodiment, the hydrogen-sensitive material is palladium. The sputtering parameter may be 15 mA/240 s.

The manufacturing method of the hydrogen sensor as described above is not only simple in manufacture, low in cost, but also widely applicable.

A method for implementing hydrogen detection based on the hydrogen sensor according to an embodiment includes the following steps.

In step S100, an incident light is irradiated onto a surface of the hydrogen-sensitive material nano structure, and an optical parameter of the hydrogen-sensitive material nanostructure is measured. The optical parameter is a resonant wavelength, a full width at half maximum value of a resonant peak, a reflectivity, a reflected light intensity, a transmittivity, a transmitted light intensity, a scattering cross-section, an extinction cross-section, an absorption cross-section or an absorbance. The resonant wavelength, the full width at half maximum value of the resonant peak, or the reflectivity at a certain wavelength of the hydrogen-sensitive material nanostructure may be measured by using an ultraviolet-visible-near-infrared spectrophotometer.

The resonant wavelength and the full width at half maximum value of the resonant peak may be determined by recording the reflectance spectrum of a certain wavelength band, and the reflectivity may be determined by recording the reflectance spectrum of a certain wavelength band or the reflectivity of a certain wavelength in a certain period of time.

It should be noted that the resonant wavelength refers to the wavelength at which the lowest point of the reflection valley of the hydrogen sensor is positioned. The full width at half maximum value of the resonant peak refers to a corresponding spectral band width when the reflectivity in a reflection valley is half of the maximum reflection drop.

In step S200, a gas containing hydrogen is introduced, the hydrogen-sensitive material nanostructure expands in volume after absorbing hydrogen, and the elastic substrate is deformed.

Specifically, the introduced hydrogen is a mixed gas of hydrogen and nitrogen. For example, 4% hydrogen is introduced, which refers to a mixed gas of hydrogen and nitrogen (the volume ratio of hydrogen to nitrogen is 4:96) is introduced. The hydrogen-sensitive material nanostructure expands in volume after hydrogen absorption, and during the expansion process, it applies stress to a surface of the elastic substrate, so that the geometry of the nano-groove on the elastic substrate 1 changes (the opening size of the groove becomes smaller), thereby further shifting the resonant wavelength of the hydrogen-sensitive material nanostructure.

In step S300, an incident light is irradiated onto a surface of the deformed hydrogen-sensitive material nanostructure, and an optical parameter of the deformed hydrogen-sensitive material nanostructure is measured.

It should be noted that the step S200 and the step S300 may be performed simultaneously, and the optical parameter and the change in the optical parameter are recorded in real time.

In step S400, a change in the relative optical parameter is obtained through measuring optical parameters of the hydrogen-sensitive material nanostructure before and after deformation, and a concentration of hydrogen is determined according to the change in the relative optical parameter.

Specifically, in the present embodiment, the change in the relative reflectivity intensity is calculated by measuring reflectivity before and after the deformation of the hydrogen-sensitive material nanostructure. And then the change in the relative reflectivity intensity is compared with a relationship information between the hydrogen concentrations and the changes in the relative reflectivity intensity, to determine the concentration of the introduced hydrogen. It should be noted that the relationship information between the hydrogen concentration and the change in the relative reflectivity intensity may be a lookup table or the like, the lookup table represents the changes in relative reflectivity intensity corresponding to different hydrogen concentrations.

The present disclosure will be further set forth by following specific examples.

Example 1

(1) At a room temperature and under a dark room condition, a polymethyl methacrylate film and a photoresist film were sequentially spin-coated on a clean quartz substrate. The polymethyl methacrylate film had a thickness of 50 nm, and the photoresist film had a thickness of 90 nm.

(2) A double beam exposure and development were performed on the photoresist, so that the photoresist layer had a nano-grating structure. The condition of double beam exposure and development was that: the incident angle of the double beam was 34.9 degrees, and the exposure time was 50 seconds, the developing time was 60 seconds, and the developing temperature was 21° C.

(3) The treated photoresist and a release agent (perfluorooctyltrichlorosilane) were placed into a vacuum vessel and then the vacuum vessel was vacuumized, and after standing the vacuumized vacuum vessel for 40 minutes, the release agent molecules were volatilized and covered onto the photoresist template.

(4) 3.4 g of vinylmethylsiloxane-dimethylsiloxane copolymers, trimethylsiloxy terminated, 100 mg of 1,3,5,7-tetravinyltetramethylcyclotetrasiloxane, and 50 mg of tetramethyldivinylsiloxane platinum complex were mixed, and then were stirred uniformly, and placed into a vacuum vessel and then the vacuum vessel was vacuumized to remove bubbles therein. Then, 1 g of hydride terminated methyhydrosiloxane dimethylsiloxane copolymer was added into the above mixture, and stirred uniformly to form a second mixed liquid.

(5) The second mixed liquid was spin-coated on photoresist template treated by the release agent, and was placed into an oven for curing. The second mixed liquid was cured at 70° C. for 20 minutes to form a second elastic substrate. The second elastic substrate had a thickness of 30 μm.

(6) A polydimethylsiloxane and a first curing agent were mixed at a mass ratio of 10:1 at a room temperature, and then were stirred uniformly to obtain a first mixed liquid. The first mixed liquid was coated on the second elastic substrate, and was placed into a vacuum vessel to remove bubbles therein.

(7) The template coated with the first mixed liquid in step (6) was placed into an oven, and was cured at 70° C. for 20 minutes to form a first elastic substrate. The first elastic substrate had a thickness of 1 mm.

(8) The composite elastic substrate formed by the first elastic substrate and the second elastic substrate positioned at the edge of the quartz plate was cut open using a clean knife. The composite elastic substrate was separated from the treated photoresist, so that a surface of the second elastic substrate away from the first elastic substrate had a nano-array structure thereon.

(9) Palladium was deposited on the second elastic substrate using a magnetron sputtering apparatus to form a hydrogen-sensitive material nanostructure. The sputtering parameter was 15 mA/240 s. The parameter of the size of the formed palladium nano-groove array was that: the period was 400 nm, the groove depth was 90 nm, the groove opening width was 260 nm, and the groove bottom width was 90 nm.

Figure 11:
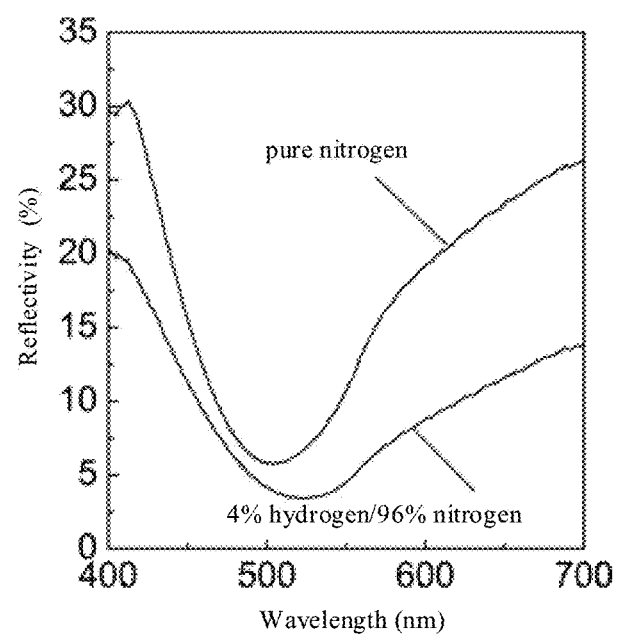
FIG. 11 is a reflectance spectrum of the hydrogen sensor obtained in Example 1 when introducing pure nitrogen and introducing 4% hydrogen.

The hydrogen sensor manufactured in Example 1 was placed into a gas flow cell, and pure nitrogen was introduced into the gas flow cell, and reflectance spectrum of the hydrogen sensor was measured by using an ultraviolet-visible-near-infrared spectrophotometer (Lambda 950, PerkinElmer). Then, 4% hydrogen (a mixed gas of hydrogen and nitrogen, with a volume ratio of hydrogen to nitrogen of 4:96) was introduced into the gas flow cell, and reflectance spectrum of the hydrogen sensor was measured by using an ultraviolet-visible-near-infrared spectrophotometer (Lambda 950, PerkinElmer), as shown in FIG. 11. By comparing the results of the two measurements, it can be inferred that the resonant wavelength of the hydrogen sensor had shifted by 20 nm and the full width at half maximum of the resonance peak was 145 nm. In addition, at a wavelength of 550 nm, the maximum value of the change in the relative reflectivity was measured to be 139%.

Example 2

The hydrogen sensor was manufactured according to the steps of Example 1, except that the parameters of the size of the nano-grating structure were: the period was 1000 nm, the groove depth was 90 nm, the groove opening width was 370 nm, and the groove bottom width was 240 nm.

Figure 12:
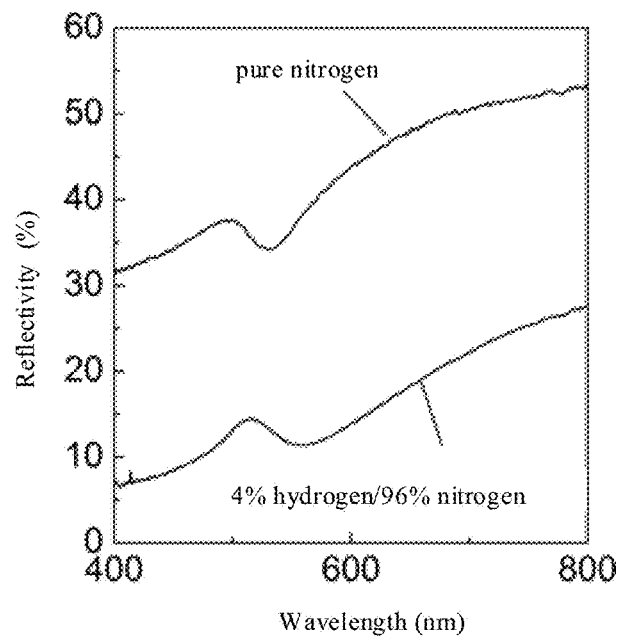
FIG. 12 is a reflectance spectrum of the hydrogen sensor obtained in Example 2 when introducing pure nitrogen and introducing 4% hydrogen.

The hydrogen sensor manufactured in Example 2 was placed into the gas flow cell, and pure nitrogen was introduced into the gas flow cell, and reflectance spectrum of the hydrogen sensor was measured by using an ultraviolet-visible-near-infrared spectrophotometer (Lambda 950, PerkinElmer). Then, 4% hydrogen (a mixed gas of hydrogen and nitrogen, with a volume ratio of hydrogen to nitrogen of 4:96) was introduced into the gas flow cell, and the reflectance spectrum of the hydrogen sensor was measured by using an ultraviolet-visible-near-infrared spectrophotometer (Lambda 950, PerkinElmer). The measurement result was as shown in FIG. 12. According to the method for measuring and calibrating the reflectance spectrum in Example 1, the resonant wavelength of the hydrogen sensor was measured to have shifted by 28 nm and the full width at half maximum of the resonance peak was 32 nm. In addition, at a wavelength of 400 nm, the maximum value of the change in the relative reflectivity was measured to be 390%.

Example 3

The hydrogen sensor was manufactured according to the steps of Example 1, except that the parameters of the size of the nano-grating structure were: the period was 500 nm, the groove depth was 90 nm, the groove opening width was 260 nm, and the groove bottom width was 90 nm.

The hydrogen sensor manufactured in Example 3 was placed into a gas flow cell, and pure nitrogen was introduced into the gas flow cell, and reflectance spectrum of the hydrogen sensor was measured by using an ultraviolet-visible-near-infrared spectrophotometer (Lambda 950, PerkinElmer). Then, 4% hydrogen (a mixed gas of hydrogen and nitrogen, with a volume ratio of hydrogen to nitrogen gas of 4:96) was introduced into the gas flow cell, and the reflectance spectrum of the hydrogen sensor was measured by using an ultraviolet-visible-near-infrared spectrophotometer (Lambda 950, PerkinElmer). According to the method for measuring and calibrating the reflectance spectrum in Example 1, the resonant wavelength of the hydrogen sensor was measured to have shifted by 18 nm and the full width at half maximum of the resonance peak was 129 nm. In addition, at a wavelength of 650 nm, the maximum value of the change in the relative reflectivity was measured to be 153%.

Example 4

The hydrogen sensor was manufactured according to the steps of Example 1, except that the parameters of the size of the nano-grating structure were: the period was 600 nm, the groove depth was 90 nm, the groove opening width was 260 nm, and the groove bottom width was 90 nm.

The hydrogen sensor manufactured in Example 4 was placed into a gas flow cell, and pure nitrogen was introduced into the gas flow cell, and reflectance spectrum of the hydrogen sensor was measured by using an ultraviolet-visible-near-infrared spectrophotometer (Lambda 950, PerkinElmer). Then, 4% hydrogen (a mixed gas of hydrogen and nitrogen gas, with a volume ratio of hydrogen to nitrogen gas of 4:96) was introduced into the gas flow cell, and the reflectance spectrum of the hydrogen sensor was measured by using an ultraviolet-visible-near-infrared spectrophotometer (Lambda 950, PerkinElmer). According to the method for measuring and calibrating the reflectance spectrum in Example 1, the resonant wavelength of the hydrogen sensor was measured to have shifted by 18 nm and the full width at half maximum of the resonance peak was 74 nm. In addition, at a wavelength of 675 nm, the maximum value of the change in the relative reflectivity was measured to be 400%.

Example 5

The hydrogen sensor was manufactured according to the steps of Example 1, except that the parameters of the size of the nano-grating structure were: the period was 700 nm, the groove depth was 90 nm, the groove opening width was 300 nm, and the groove bottom width was 200 nm.

The hydrogen sensor manufactured in Example 5 was placed into a gas flow cell, and pure nitrogen was introduced into the gas flow cell, and the reflectance spectrum of the hydrogen sensor was measured by using an ultraviolet-visible-near-infrared spectrophotometer (Lambda 950, PerkinElmer). Then, 4% hydrogen (a mixed gas of hydrogen and nitrogen gas, with a volume ratio of hydrogen to nitrogen gas of 4:96) was introduced into the gas flow cell, and the reflectance spectrum of the hydrogen sensor was measured by using an ultraviolet-visible-near-infrared spectrophotometer (Lambda 950, PerkinElmer). According to the method for measuring and calibrating the reflectance spectrum in Example 1, the resonant wavelength of the hydrogen sensor was measured to have shifted by 15 nm and the full width at half maximum of the resonance peak was 79 nm. In addition, at a wavelength of 790 nm, the maximum value of the change in the relative reflectivity was measured to be 192%.

Example 6

(1) At a room temperature and under a dark room condition, a polymethyl methacrylate film and a photoresist film were sequentially spin-coated on a clean quartz substrate. The polymethyl methacrylate film had a thickness of 50 nm, and the photoresist film had a thickness of 90 nm.

(2) A double beam exposure and development was performed on the photoresist, so that the photoresist layer had a nano-grating structure. The conditions of the double beam exposure and development were: the incident angle of the double beam was 34.9 degrees, the exposure time was 50 seconds, the developing time was 60 seconds, and the developing temperature was 21° C.

(3) Both of the treated photoresist and the release agent perfluorooctyltrichlorosilane were placed into a vacuum vessel and then the vacuum vessel was vacuumized, and after standing the vacuum vessel for 40 minutes, the release agent molecules were volatilized and covered onto the photoresist template.

(4) A polydimethylsiloxane and a curing agent were mixed at a mass ratio of 10:1 at a room temperature, and then were stirred uniformly to obtain a mixed liquid, and the mixed liquid was coated on the nano-grating structure, and was placed into a vacuum vessel to remove bubbles.

(5) The template coated with the mixed liquid in step (4) was placed into an oven, and was cured at 70° C. for 20 minutes to form an elastic substrate. The elastic substrate had a thickness of 1 mm.

(6) The elastic substrate positioned at the edge of the quartz plate was cut open using a clean knife, and the elastic substrate was separated from the treated photoresist, so that a surface of the elastic substrate had nanoarray structure thereon.

(7) Palladium was deposited on the elastic substrate using a magnetron sputtering apparatus to form a hydrogen-sensitive material nanostructure. The sputtering parameter was 15 mA/240 s. The parameter of the size of the formed palladium nano-groove array was that: the period was 400 nm, the groove depth was 90 nm, the groove opening width was 280 nm, and the groove bottom width was 100 nm.

Figure 13:
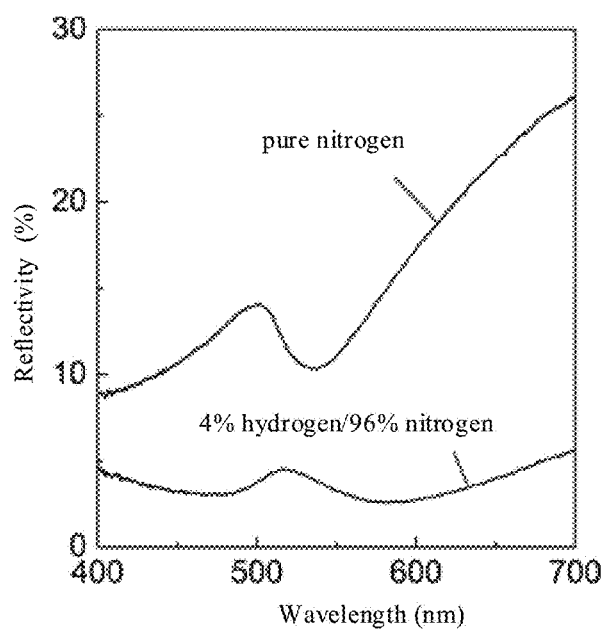
FIG. 13 is a reflectance spectrum of the hydrogen sensor obtained in Example 6 when introducing pure nitrogen and introducing 4% hydrogen.

The hydrogen sensor manufactured in Example 6 was placed into a gas flow cell, and pure nitrogen was introduced into the gas flow cell, and reflectance spectrum of the hydrogen sensor was measured by using an ultraviolet-visible-near-infrared spectrophotometer (Lambda 950, PerkinElmer). Then, 4% hydrogen (a mixed gas of hydrogen and nitrogen, with a volume ratio of hydrogen to nitrogen of 4:96) was introduced into the gas flow cell, and reflectance spectrum of the hydrogen sensor was measured by using an ultraviolet-visible-near-infrared spectrophotometer (Lambda 950, PerkinElmer). The measurement result was as shown in FIG. 13. According to the method for measuring and calibrating the reflectance spectrum in Example 1, the resonant wavelength of the hydrogen sensor was measured to have shifted by 50 nm and the full width at half maximum of the resonance peak was 45 nm. In addition, at a wavelength of 600 nm, the maximum value of the change in the relative reflectivity was measured to be 535%.

Spectral Measurement

The hydrogen sensor was placed into a gas flow cell, and reflectance spectrum thereof was measured by using an ultraviolet spectrophotometer (Lambda 950, PerkinElmer). The detector was at a distance of 32 cm from the hydrogen sensor, and a size of a light collection area was 7 mm*7 mm. Firstly, a silver mirror was placed into the gas flow cell to measure the reflectivity of the hydrogen sensor. The errors causing by the reflection of the detecting light by the glass lens in the gas flow cell was calibrated by using the reflectivity of the silver mirror in the flow cell. The calibration formula is $$R = \frac{R_S - R_B}{R_{Ag} - R_B},$$

where Rs is the reflectivity of the hydrogen sensor, $R_{Ag}$ is the reflectivity of the silver mirror, and RB is the reflectivity of the background. The calculation formula of the change in the relative reflectivity is: $\Delta R_{rel} = (R_{0\%} - R_{i\%})/R_{i\%}$, i is greater than 0 and less than or equal to 4, $\Delta R_{rel}$ is the change in the relative reflectivity, $R_{0\%}$ is the reflectivity before hydrogen introduction, $R_{i\%}$ is the reflectivity of hydrogen being introduced and having a concentration of i %.

Figure 14:
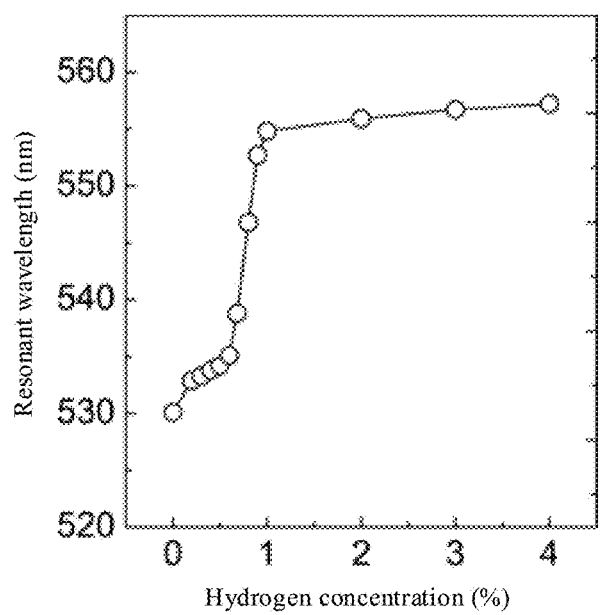
FIG. 14 is a graph showing the relationship between the resonant wavelength of the hydrogen sensor and the hydrogen concentration obtained in Example 2.

Referring again to FIG. 14, FIG. 14 is a graph showing the relationship between the resonant wavelength and the hydrogen concentration of the hydrogen sensor obtained in Example 2. The hydrogen sensor manufactured in Example 2 was placed into a gas flow cell, and different concentrations of hydrogen (the other component of the mixed gas is nitrogen) were introduced into the gas flow cell, and the reflectance spectrums of the hydrogen sensor were measured by using an ultraviolet-visible-near-infrared spectrophotometer (Lambda 950, PerkinElmer). The concentrations of the hydrogen were 0%, 0.2%, 0.3%, 0.4%, 0.5%, 0.6%, 0.7%, 0.8%, 0.9%, 1%, 2%, 3% and 4%, respectively. It can be seen from the figure that the linear response range of the resonant wavelength of the hydrogen sensor was between 0.6% and 1% of the hydrogen concentration, and it can be seen that the hydrogen sensor had a higher sensitivity.

Figure 15:
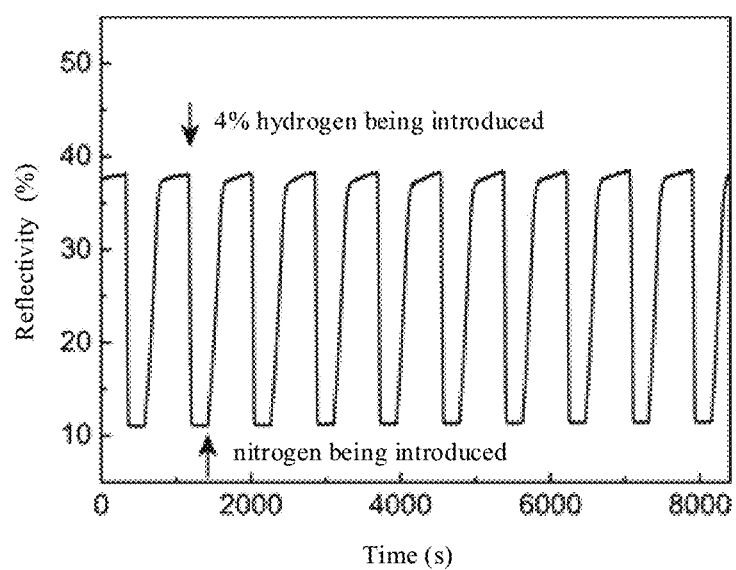
FIG. 15 is a graph showing the change in reflectivity with time of a hydrogen sensor obtained in Example 2 when introducing 10 cycles of 4% hydrogen and pure nitrogen.

Please refer to FIG. 15, FIG. 15 is a graph showing the change in reflectivity with time of a hydrogen sensor obtained in Example 2 when introducing 10 cycles of 4% hydrogen and pure nitrogen. The hydrogen sensor manufactured in Example 2 was placed into a gas flow cell, and pure nitrogen was introduced into the gas flow cell under a detecting light with a wavelength of 560 nm, and the reflectivity of the hydrogen sensor was measured by using an ultraviolet-visible-near-infrared spectrophotometer (Lambda 950, PerkinElmer). Then, 4% hydrogen (a mixed gas of hydrogen and nitrogen gas, with a volume ratio of hydrogen to nitrogen of 4:96) was introduced into the gas flow cell, and the reflectivity of the hydrogen sensor was measured by using an ultraviolet-visible-near-infrared spectrophotometer (Lambda 950, PerkinElmer). The above steps were repeated for 10 cycles. It can be seen from the figures that the reflectivity of the hydrogen sensor under pure nitrogen and 4% hydrogen remained stable, and it can be seen that the hydrogen sensor had a relatively good repeatability.

The technical features of the above-described embodiments may be combined arbitrarily. To simplify the description, not all the possible combinations of the technical features in the above embodiments are described. However, all of the combinations of these technical features should be considered as being within the scope of the present disclosure, as long as there are no contradictions in such combinations.

The above embodiments only represent several embodiments of the present disclosure, and the description thereof is relatively specific and detailed, but they should not be construed as limiting the scope of the present disclosure. It should be noted that, for those skilled in the art, several variations and improvements may be made without departing from the concept of the present disclosure, and these are all within the protection scope of the present disclosure. Therefore, the protection scope of the present disclosure shall be defined by the appended claims.

What is claimed is:

1. A hydrogen sensor, comprising an elastic substrate and a hydrogen-sensitive material nanostructure positioned on the elastic substrate, a surface of the elastic substrate adjacent to the hydrogen-sensitive material nanostructure having a nanoarray structure, the hydrogen-sensitive material nanostructure and the nanoarray structure being complementary to each other.

2. The hydrogen sensor according to claim 1, wherein a material used in the hydrogen-sensitive material nanostructure is at least one selected from the group consisting of palladium, magnesium, yttrium, and nickel-magnesium alloy.

3. The hydrogen sensor according to claim 1, wherein the hydrogen-sensitive material nanostructure is selected from a one-dimensional nanoarray or a two-dimensional nanoarray.

4. The hydrogen sensor according to claim 3, wherein the hydrogen-sensitive material nanostructure is selected from a one-dimensional nano-groove array, and the hydrogen-sensitive material nanostructure has a period of 300 nm to 100000 nm.

5. The hydrogen sensor according to claim 4, wherein a groove in the one-dimensional nano-groove array has a depth of 50 nm to 1000 nm.

6. The hydrogen sensor according to claim 4, wherein a groove in the one-dimensional nano-groove array has an opening width of 150 nm to 400 nm.

7. The hydrogen sensor according to claim 1, wherein the elastic substrate comprises a first elastic substrate and a second elastic substrate which are sequentially laminated, and a Young's modulus of the second elastic substrate is greater than a Young's modulus of the first elastic substrate.

8. The hydrogen sensor according to claim 7, wherein the first elastic substrate has a thickness of 0.5 mm to 10 mm, and the second elastic substrate has a thickness of 5 μm to 100 μm.

* * * * *